United States Patent
Coelingh Bennink et al.

(10) Patent No.: US 8,026,228 B2
(45) Date of Patent: Sep. 27, 2011

(54) ESTROGENIC COMPOUNDS IN COMBINATION WITH PROGESTOGENIC COMPOUNDS IN HORMONE-REPLACEMENT THERAPY

(75) Inventors: Herman Jan Tijmen Coelingh Bennink, Driebergen (NL); Evert Johannes Bunschoten, Heesch (NL); Christian Franz Holinka, New York, NY (US)

(73) Assignee: Pantarhei Bioscience B.V. (NL)

( * ) Notice: Subject to any disclaimer, the term of this patent is extended or adjusted under 35 U.S.C. 154(b) by 1043 days.

(21) Appl. No.: 10/495,707

(22) PCT Filed: May 23, 2002

(86) PCT No.: PCT/NL02/00332
§ 371 (c)(1), (2), (4) Date: Nov. 16, 2004

(87) PCT Pub. No.: WO03/041718
PCT Pub. Date: May 22, 2003

(65) Prior Publication Data
US 2005/0070488 A1    Mar. 31, 2005

(30) Foreign Application Priority Data

Nov. 15, 2001  (EP) ................................. 01204377
Feb. 21, 2002  (EP) ................................. 02075695

(51) Int. Cl.
*A01N 45/00* (2006.01)
*A61K 31/56* (2006.01)

(52) U.S. Cl. ....... 514/169; 514/170; 514/171; 514/10.2; 514/874

(58) Field of Classification Search ............... 514/182, 514/10.2, 169–171, 874; 424/400
See application file for complete search history.

(56) References Cited

U.S. PATENT DOCUMENTS

| | | | |
|---|---|---|---|
| 3,440,320 A | 4/1969 | Sackler et al. | |
| 3,797,494 A | 3/1974 | Zaffaroni | |
| 4,460,372 A | 7/1984 | Campbell et al. | |
| 4,573,996 A | 3/1986 | Kwiatek et al. | |
| 4,624,665 A | 11/1986 | Nuwayser | |
| 4,722,941 A | 2/1988 | Eckert et al. | |
| 4,762,717 A | 8/1988 | Crowley, Jr. | |
| 4,937,238 A | 6/1990 | Lemon | |
| 5,063,507 A | 11/1991 | Lindsey et al. | |
| 5,130,137 A | 7/1992 | Crowley, Jr. | |
| 5,211,952 A | 5/1993 | Spicer et al. | |
| 5,223,261 A | 6/1993 | Nelson et al. | |
| 5,340,584 A | 8/1994 | Spicer et al. | |
| 5,340,585 A | 8/1994 | Pike et al. | |
| 5,340,586 A | 8/1994 | Pike et al. | |
| 5,468,736 A | 11/1995 | Hodgen | |
| 5,633,242 A | 5/1997 | Oettel et al. | |
| 5,662,927 A * | 9/1997 | Ehrlich et al. | 424/449 |
| 5,827,843 A | 10/1998 | Koninckx | |
| 6,214,815 B1 * | 4/2001 | Shangold et al. | 514/170 |
| 6,500,814 B1 | 12/2002 | Hesch | |
| 2002/0013304 A1 * | 1/2002 | Wilson et al. | 514/177 |
| 2002/0183299 A1 | 12/2002 | Voskuhl | |

FOREIGN PATENT DOCUMENTS

| | | |
|---|---|---|
| DE | 23 36 433 A | 4/1975 |
| DE | 23 36 434 A | 4/1975 |
| DE | 0 402 950 A | 12/1975 |
| DE | 2426779 A1 | 12/1975 |
| DE | 19917930 A1 | 10/2000 |
| EP | 468690 A | 7/1991 |
| EP | 1700602 A1 | 5/2001 |
| WO | WO 92 18107 A | 10/1992 |

(Continued)

OTHER PUBLICATIONS

Hill et al., American Journal of Obstetrics and Gynecology, 2000, 183(6), 1456-1461.*
Vehkavaara, S., Differential Effects of Oral and Transdermal Estrogen Replacement Therapy on Endothelial Function in Postmenopausal Women, Circulation, 2000, American Heart Association, vol. 102; 2687-2693.*

(Continued)

*Primary Examiner* — Rebecca Prouty
*Assistant Examiner* — Danielle Sullivan
(74) *Attorney, Agent, or Firm* — The Webb Law Firm

(57) ABSTRACT

One aspect of the present invention relates to a method of hormone replacement in mammals, which method comprises the oral administration of an estrogenic component and a progestogenic component to a mammal in an effective amount to prevent or treat symptoms of hypoestrogenism, wherein the estrogenic component is selected from the group consisting of substances represented by the above formula in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; and no more than 3 of $R_1$, $R_2$, $R_3$, $R_4$ are hydrogen atoms; precursors capable of liberating a substance according to the aforementioned formula when used in the present method; and mixtures of one or more of the aforementioned substances and/or precursors. Another aspect of the invention concerns a pharmaceutical kit comprising oral dosage units that contain the aforementioned estrogenic component and a progestogenic component as well as an androgenic component.

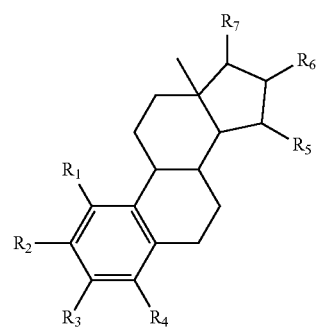

14 Claims, 4 Drawing Sheets

FOREIGN PATENT DOCUMENTS

| WO | 9426207 | 11/1994 |
|---|---|---|
| WO | 9603929 A1 | 2/1996 |
| WO | 9858657 A1 | 12/1998 |
| WO | 0062753 | 10/2000 |
| WO | WO 00/73416 | 12/2000 |
| WO | WO 01 30357 A | 5/2001 |
| WO | 0185154 A2 | 11/2001 |

OTHER PUBLICATIONS

Giltay, E.J., Oral, but Not Transdermal, Administration of Estrogens Lowers Tissue-Type Plasminogen Activator Levels in Humans Without Affecting Endothelial Synthesis, Arteriosclerosis, Thrombosis, and Vascular Biology, 2000, American Heart Association, vol. 20; 1396-1403.*

Allen et al., An Ovarian Hormone: Preliminary Report on Its Localization, Extraction and Partial Purification, and Action in Test Animals, JAMA, Sep. 8, 1923, vol. 81, pp. 819-821.

Allen et al., The Induction of a Sexually Mature Condition in Immature Females by Injection of the Ovarian Follicular Hormone, Am. J. Physiol., 1924, vol. 69, pp. 577-588.

Fishman, Fate of 15a-Hydroxyestriol-$^3$H in Adult Man, J. Clin. Endocrinol. Metab., 1970, vol. 31, pp. 436-438.

Jones et al., The Effects of Various Steroids on the Vaginal Histology in the Rat, Fertility and Sterility, Apr. 1973, vol. 24, No. 4, pp. 284-291.

Tulchinsky et al., Plasma Esterol as an Index of Fetal Well-Being, J. Clin. Endrocrinol. Metab., 1975, vol. 40. pp. 560-567.

Tseng et al., Competition of Esterol and Ethynylestradiol with Estradiol for Nuclear Binding in Human Endometrium, Journal of Steroid Biochemistry, 1976, vol. 7, pp. 817-822.

Martucci et al., Uterine Estrogen Receptor Binding of Cathecholestrogens and of Esterol (1,2,5(10)-Estratriene-3,15a,16a,17 β-Tetrol), Steroids, Mar. 1976, vol. 27, No. 3, pp. 325-333.

Martucci et al., Direction of Estradiol Metabolism as a Control of its Hormonal Action—Uterotrophic Activity of Estradiol Metabolites, Endrocrin., 1977, vol. 101, pp. 1709-1715.

Tseng et al., Heterogeneity of Saturable Estradiol Binding Sites in Nuclei of Human Endometrium Esterol Studies, Steroid Biochem., 1978, vol. 9, pp. 1145-1148.

Jozan et al., Different Effects of Oestradiol, Oestriol, Oestrol and of Oestrone on Human Breast Cancer Cells (MCF-7) in Long Term Tissue Culture, Acta Endocrinologica, 1981, vol. 98, pp. 73-80.

Hammond et al, A Versatile Method for the Determination of Serum Cortisol Binding Globulin and Sex Hormone Binding Globulin Binding Capacities, 1983, vol. 132, pp. 101-110.

Levine et al., Uterine Vascular Effects of Esterol in Nonpregnant Ewes, Am. J. Obstet. Gynecol., 1984, vol. 148, No. 73. pp. 735-738.

Elger et al., Sulfamates of Various Estrogens are Prodrugs with Increased Systemic and Reduced Hepatic Estrogenicity at Oral Application, J. Steroid Biochem. Molec. Biol., 1995, vol. 55, No. 3 / 4, pp. 395-403.

Murphy et al., Endometrial Effects of Long-Term Low-Dose Administration of RU486, Fertility and Sterility, Apr. 1995, vol. 63, No. 4, pp. 761-766.

Reel et al., Survey and Assessment of Mammalian Estrogen Biological Assays for Hazard Characterization, Fundamental and Applied Toxicology, 1996, vol. 34, pp. 288-305.

Beral et al., Use of HRT and the Subsequent Risk of Cancer, Journal of Epidemiology and Biostatistics, 1999, vol. 4, No. 3, pp. 191-215.

Tavani et al., The Adverse Effects of Hormone Replacement Therapy, Drugs & Aging, May 1999, vol. 14, No. 5, pp. 347-357.

Pike et al., Progestins and Menopause: Epidemiological Studies of Risks of Endometrial and Breast Cancer, Steroids, 2000, vol. 65, pp. 359-664.

Avvakumov et al., Steroid-binding Specificity of Human Sex Hormon-binding Globulin is Influenced by Occupancy of a Zinc-binding Site, The Journal of Biological Chemistry, Aug. 25, 2000, vol. 275, No. 34, pp. 25920-25925.

H. Seeger, et al., "The Inhibitory Effect of Endogenous Estrogen Metabolites on Copper-Mediated in Vitro Oxidation of LDL," International Journal of Clinical Pharmacology and Therapeutics. Germany Jul. 1998, vol. 36, No. 7, Jul. 1998, pp. 383-385.

C. F. Holinka et al., "In-Vivo Effects of Estetrol on the Immature Rat Uterus," Biology of Reproduction, vol. 20, No. 2, 1979, pp. 242-246.

C. F. Holinka et al., "Comparison of Effects of Estetrol and Tamoxifen With Those of Estriol and Estradiol on the Immature Rat Uterus," Biology of Reproduction, vol. 22, No. 4, 1980, pp. 913-926.

Visser et al., "In vitro effects of estetrol on receptor binding, drug targets and human liver cell metabolism," Climacteric (2008) 11(1) Appx. II: 1-5.

Visser et al., "First human exposure to exogenous single-dose oral estetrol in early postmenopausal women," Climacteric (2008) 11(1): 1-10.

Visser et al., "Clinical applications of estetrol," J. of Steroid Biochem and Molecular Biol. (2009) 114: 85-89.

Coelingh Bennink et al., "Oral bioavailability and bone sparing effects of estetrol in an osteoporosis model," Climacteric (2008) 11 (Supp 3): 1-13.

Albertazzi Paola et al., "The Effect of Tibolone Versus Continuous Combined Norethisterone Acetate and Oestradiol on Memory, Libido and Mood of Postmenopausal Women: A Pilot study"; Database Biosis 'Online|; Oct. 31, 2000; pp. 223-229; vol. 36, No. 3; Biosciences Information Service, Philadelphia, PA., U.S.

Jansson et al., "Estrogen Induces a Potent Suppression of Experimental Autoimmune Encephalomyelitis and Collagen-Induced Arthritis in Mice", Journal of Neuroimmunology, Elsevier Science Publishers BV XX, 1994, vol. 53, No. 2, pp. 203-207.

Lab Tests Online (www.labtestsonline.org/understanding/conditions/autoimmune.html) retrieved on Oct. 15, 2009.

www.tiscali.co.uk/lifestyle/healthfitness/health_advice/netdoctor/archive/000489.html, retrieved on Oct. 15, 2009.

MedlinePlus Medical Encyclopedia: Mutiple Sclerosis, retrieved on Mar. 28, 2008 via www.nlm.nih.gov/medlineplus/ency/article/000737.htm, dated on Aug. 6, 2007, p. 1 and 2; also see WebMD: Multiple Sclerosis—Prevention, retrieved on Mar. 28, 2008 via www.webmd.com/multiple-sclerosis/tc/multiple-sclerosis-ms-prevention, dated on Mar. 23, 2006.

MedlinePlus Medical Encyclopedia: rheumatoid arthritis, retrieved on Mar. 28, 2008 via www.nlm.nih.gov/medlineplus/ency/article/000431.htm, dated on Jul. 27, 2007, p. 1-2 and 4; also WebMD: Rheumatoid Arthritis —Prevention, retrieved on Mar. 28, 2008 via www.webmd.com/rheumatoid-arthritis/tc/rheumatoid-arthritis-prevention, dated on Aug. 23, 2006.

Mueck et al., "Angio and Anti-Angiogenetic Effects of Estradiol and its Metabolites", J. Clin. Basic Cardiol., 2001, pp. 153-155, vol. 4, No. 2.

Shah et al., "Estrogen and Skin. An Overview", Am. J. Clin. Dermatol., 2001, pp. 143-150, vol. 2, No. 3.

Sitruk-Ware et al., "Local Hormonal Treatment for Urogenital Atrophy After Menopause", Shweiz. Rundsch, Med. Praxis, 1997, pp. 1245-1248, vol. 86, No. 33, and Sitruk-Ware, English Translation, 1997. Praxis, Schweizerische Rundschau fur Medizin, vol. 86, No. 33, pp. 1-13, French.

Schmidt et al., "Treatment of Skin Aging with Topical Estrogens", Int. J. Dermatol., 1996, pp. 669-674, vol. 35, No. 9.

Younglai et al., Journal of Clinical Endocrinology and Metabolism, 1968, vol. 28, Issue 11, pp. 1611-1617.

Webster Ninth New Collegiate Dictionary, 2000, Definition of Prevention, p. 1.

Willhite et al., Pharmacotherapy, 2001, vol. 21, Issue 4, pp. 464-480.

Kuipers et al., "Enterohepatic Circulation in the Rat", Gastroenterol., vol. 88, pp. 403-411 (1985).

Schwartz, "A Model for the Regulation of Ovulation in the Rat", Recent Prog. Horm. Res., vol. 25, pp. 1-55, (1969).

Beattie et al., "The Differential Effects of Diestrous Progestogen Administration on Proestrous Gonadotrophin Levels, Endocrinol", vol. 97, pp. 885-890, (1975).

De Visser et al., Endocrinological Studies with (7a, 17 a)-17-Hydroxy-7-me norpregn-5(10)-en-20-yn-3-one (Org OD 14), Arzneim, Forsh., vol. 34, pp. 1010-1020, (1984).

Medline Plus: Medical Encyclopedia: Ovarian cancer retrieved online on Aug. 9, 2007 from the internet: https://www.nlm.nih.gov/medlineplus/ovariancancer.html, p. 1 dated Jul. 31, 2007.

Coelingh-Bennink et al., "Estetrol review: profile and potential clinical applications", International Menopause Society, Climateric, vol. 11, (Suppl 1), pp. 47-58 (2008).

Speroff et al., Clinical Gynecologic Endocrinology and Infertility, Seventh Edition, p. 270 (partial), 2005.

White et al., "The pharmacokinetics of Intravenous Estradiol: A Preliminary Study", Pharmacotherapy, vol. 18, pp. 1343-1346, (1998) (Abstract).

Hammond et al., "Estetrol does not bind sex hormone binding globulin or increase its production by human HepG2 cells", International Menopause Society, Climateric, vol. 11, (Suppl. 1), pp. 41-46, (2008).

Breast Cancer Prevention retrieved online Aug. 7, 2007 from the internet; http://www.cancer.gov/cancertopics/pdq/prevention/breast/Patient/p. 3.

Prophylactic definition—Medical Dictionary of Popular Medical Terms; retrieved on Mar. 14, 2008 via www.medterms.com/script/main/art.asp?articlekey+11902.

Zips et al., in vivo, 2005, vol. 19, pp. 1-8.

Holinka et al., Biology of Reproduction, 1980, vol. 22, pp. 913-926.

Martucci et al., "Impact of Continuously Administered Catechol Estrogens on Uterine Growth and Luteinizing Hormone Secretion", Endocrinology (Dec. 1979), vol. 105, No. 6, pp. 1288-1292.

Weigert et al., "Comparison of Stimulation with Clomiphenes Citrate in Combination with Recombinant Follicle Stimulating Hormone and Recombinant Luteinizing Hormone to Stimulation with a Gonadotropin-Releasing Hormone Agonist Protocol. A prospective Randomized Study", Fertility and Sterility, (Jul. 2002), vol. 78, No. 1, pp. 34-39.

Trotter et al., "Effects of Postnatal Estradiol and Progesterone Replacement in Extremely Preterm Infants", J. Clin. Endocrinol Metab., (Dec. 1999), vol. 84, No. 12, pp. 4531-4535.

Shanklin et al., "Aqueous Estrogens in the Management of Respiratory Distress Syndrome", J. Reprod. Med. (Aug. 1970), vol. 5, No. 2, pp. 53-71.

Chemical Abstracts Service, Columbus Ohio, US: Jakowicki, "Evaluation of Estriol Level in the Amniotic Fluid in Prolonged Pregnancy", XP002458625, 1977.

Gorwill et al., "Unconjugated Serum Oestriol Levels in Mother and Baby with Meconium Staining of the Amniotic Fluid", Br. J. Obstet. Gynaecol. (Aug. 1978), vol. 85, No. 8, pp. 602-604.

Fogary, Jr., "Postmaturity", J. Am. Osteopath. Assoc., (Jan. 1976), vol. 75, No. 5, pp. 512-517.

Office Action mailed on Jan. 11, 2008 in U.S. Appl. No. 10/478,262.
Office Action mailed on May 15, 2008 in U.S. Appl. No. 10/478,262.
Office Action mailed on Feb. 19, 2009 in U.S. Appl. No. 10/478,262.
Office Action mailed on Jun. 9, 2009 in U.S. Appl. No. 10/478,262.
Office Action mailed on Nov. 18, 2008 in U.S. Appl. No. 10/478,264.
Office Action mailed on May 22, 2009 in U.S. Appl. No. 10/478,264.
Office Action mailed on Mar. 17, 2008 in U.S. Appl. No. 10/478,357.
Office Action mailed on May 16, 2008 in U.S. Appl. No. 10/478,357.
Office Action mailed on Dec. 16, 2008 in U.S. Appl. No. 10/478,357.
Office Action mailed on May 28, 2009 in U.S. Appl. No. 10/478,357.
Office Action mailed on Apr. 6, 2007 in U.S. Appl. No. 10/478,365.
Office Action mailed on Sep. 7, 2007 in U.S. Appl. No. 10/478,365.
Office Action mailed on Apr. 1, 2008 in U.S. Appl. No. 10/478,365.
Office Action mailed on Jun. 8, 2009 in U.S. Appl. No. 10/478,365.
Office Action mailed on Oct. 15, 2007 in U.S. Appl. No. 10/517,509.
Office Action mailed on Dec. 19, 2007 in U.S. Appl. No. 10/517,509.
Office Action mailed on Mar. 26, 2008 in U.S. Appl. No. 10/517,509.
Office Action mailed on Jan. 5, 2009 in U.S. Appl. No. 10/517,509.
Office Action mailed on Aug. 18, 2009 in U.S. Appl. No. 10/517,509.
Office Action mailed on Apr. 3, 2007 in U.S. Appl. No. 10/517,686.
Office Action mailed on Aug. 9, 2007 in U.S. Appl. No. 10/517,686.
Office Action mailed on Apr. 4, 2008 in U.S. Appl. No. 10/517,686.
Office Action mailed on May 29, 2009 in U.S. Appl. No. 10/517,686.
Office Action mailed on Apr. 23, 2007 in U.S. Appl. No. 10/521,040.
Office Action mailed on Aug. 17, 2007 in U.S. Appl. No. 10/521,040.
Office Action mailed on Apr. 2, 2008 in U.S. Appl. No. 10/521,040.
Office Action mailed on Jun. 1, 2009 in U.S. Appl. No. 10/521,040.

* cited by examiner

ESTROGENIC COMPOUNDS IN COMBINATION WITH PROGESTOGENIC COMPOUNDS IN HORMONE-REPLACEMENT THERAPY

TECHNICAL FIELD OF THE INVENTION

The present invention relates to a method of hormone replacement in mammals. More particularly the invention is concerned with a method of hormone replacement that comprises the oral administration to a mammal of a combination of an estrogenic component and a progestogenic component in an effective amount to prevent or treat symptoms of hypoestrogenism.

BACKGROUND OF THE INVENTION

In hormone replacement therapy (HRT), sometimes also referred to as estrogen replacement therapy, estrogens are administered to prevent or treat symptoms resulting from estrogen deficiency or hypoestrogenism. Hypoestrogenism can occur in both females and males, and can lead to disorders and ailments such as osteoporosis (loss of bone mass), arteriosclerosis, climacteric symptoms such as hot flushes (flashes), sweats, urogenital atrophy, mood disturbances, insomnia, palpitations. Estrogen deficiency has also been associated with cognitive disturbances and Alzheimer's disease.

Hypoestrogenism, and in particular chronic hypoestrogenism, is frequently observed in (peri-)menopausal and post-menopausal women. However, it can also result from hypogonadism or castration, as well as from primary ovarian failure, treatment of e.g. breast cancer with aromatase inhibitor and gonadotropin-releasing hormone analogue treatment of benign gynaecological diseases such as endometriosis, adenomyosis, uterine fibroids (leiomyomas), dysmenorrhoea, menorrhagia and metrorrhagia.

HRT employs continuous administration of effective amounts of an estrogen for prolonged periods of time. The administration of estrogens has been associated, however, with endometrial proliferation in women and it is now widely accepted that "unopposed" estrogen therapy substantially increases the risk of endometrial cancer (Cushing et al., 1998. Obstet. Gynecol. 91, 35-39; Tavani et al., 1999. Drugs Aging, 14, 347-357). There is also evidence of a significant increase in breast cancer with long-term (10-15 years) use of estrogen therapy (Tavani et al., 1999. Drugs Aging, 14, 347-357; Pike et al., 2000. Steroids, 65, 659-664).

In order to counteract the negative effects of unopposed estrogen therapy, adjunctive progestogen treatment is nowadays commonly applied. Regular progestogen administration is believed to inhibit the continual estrogen stimulation of the endometrium through an anti-proliferative effect and appears to reduce the incidence of endometrial carcinoma in post-menopausal women receiving estrogen replacement therapy (Beral et al., 1999. J. Epidemiol. Biostat., 4, 191-210). Such an adjunctive treatment, generally using synthetic progestogens, is given either in continuous combined regimens with estrogen, or added sequentially, typically for about 14 days each month, to continuous estrogen treatment.

Endogenous and exogenous estrogens fulfil important central nervous and metabolic functions in the female organism: normal estrogen levels make a decisive contribution to a woman's well-being. Notwithstanding the widespread use of estrogens in HRT methods, there are still some unsolved problems. Known estrogens, in particular the biogenic estrogens (i.e. estrogens naturally occurring in the human body), show serious pharmacokinetic deficits. Biogenic estrogens such as estradiol, estrone, estrone sulphate, esters of estradiol and estriol become bioavailable only to a very low degree when taken orally. This degree may vary so much from person to person that general dosage recommendations cannot be given. Fast elimination of these estrogens from the blood is another related problem. For instance, for the main human biogenic estrogen 17β-estradiol the half-life is around 1 hour. As a result, between separate (daily) administration events, blood serum levels of such biogenic estrogens tend to fluctuate considerably. Thus, shortly after administration the serum concentration is usually several times higher than the optimum concentration. In addition, if the next administration event is delayed, serum concentrations will quickly decrease to a level where the estrogen is no longer physiologically active.

The most important synthetically altered estrogenic steroid is 17α-ethinyl estradiol (EE). This estrogen is hardly used in HRT methods because prolonged administration of EE has been associated with an increased risk of thromboembolism, which is deemed to be particularly detrimental in menopausal and post-menopausal females. Apart from EE, mestranol has been used in a few cases; mestranol is a "prodrug" that is metabolised to EE in the organism. When applied orally to humans, EE has a much better bioavailability than the biogenic estrogens mentioned above, but its oral bioavailability varies to a large extent from individual to individual. Several authors have pointed to this as well as to the fact that concentrations in the blood proved to be highly fluctuating after oral application of this substance.

In addition to pharmacokinetic problems, the known estrogens also show pharmacodynamic deficits. After resorption from the intestinal lumen, orally applied active ingredients enter the organism via the liver. This fact is of specific importance for estrogenic agents as the liver is a target organ for estrogens; oral intake of estrogens results in strong estrogenic effects in the liver. The secretion activity that is controlled by estrogens in the human liver includes increased synthesis of transport proteins CBG, SHBG, TBG, several factors that are important for the physiology of blood clotting, and lipoproteins. If biogenic estrogens are introduced to the female organism while avoiding passage through the liver (e.g. by transdermal application), the liver functions mentioned remain largely unchanged. Therapeutically equivalent doses of biogenic estrogens, when applied orally, result in clear responses of hepatic parameters, such as increase of SHBG, CBG, angiotensinogen and HDL (high density lipoprotein). These hepatic effects of estrogens are also observed when equine estrogen formulations (so-called conjugated estrogens) are used. Ethinyl estradiol and diethylstilbestrol (DES) have an even greater hepatic estrogenicity. Elger et al., J. Steroid Biochem. Molec. Biol. (1995), 55(3/4), 395-403, have reported that EE or DES have much higher hepatocellular than systemic estrogenicity: in relation to FSH-secretion inhibitory activity these estrogens are 4-18 times more active in the liver than estrone sulfate.

The aforementioned deficits are of considerable clinical significance when commonly known biogenic and synthetic estrogens are applied. Consequently, there is an as yet unmet need for estrogens that do not display these deficits and which can suitably be administered orally in HRT methods to effectively replace endogenous ovarian secretion of estradiol, i.e. to treat or prevent symptoms of hypoestrogenism.

SUMMARY OF THE INVENTION

The inventors have surprisingly found that these objectives are met by estrogenic substances that are represented by the following formula

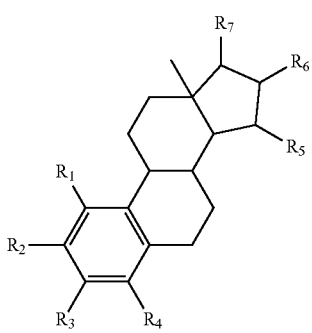

in which formula $R_1$, $R_2$, $R_3$, $R_4$ independently are a hydrogen atom, a hydroxy group or an alkoxy group with 1-5 carbon atoms; each of $R_5$, $R_6$, $R_7$ is a hydroxy group; and no more than 3 of $R_1$, $R_2$, $R_3$, $R_4$ are hydrogen atoms.

A known representative of this group of estrogenic substances is 1,3,5(10)-estratrien-3,15α,16α,17β-tetrol, also known by the names of estetrol, oestetrol and 15α-hydroxyestriol. Estetrol is an estrogen that is produced by the fetal liver during human pregnancy. Unconjugated estetrol levels in maternal plasma peak at about 1.2 ng/ml at term pregnancy and are about 12 times higher in fetal than in maternal plasma (Tulchinsky et al., 1975. J. Clin. Endocrinol. Metab., 40, 560-567).

In 1970, Fishman et al., "Fate of 15α-hydroxyestriol-$^3$H in Adult Man", J Clin Endocrinol Metab (1970) 31, 436-438, reported the results of a study wherein tritium labeled 15α-hydroxyestriol (estetrol) was administered intravenously to two adult women. It was found that the estetrol was rapidly and completely excreted in urine as the glucosiduronate and that virtually no metabolism except for conjugation took place.

Between 1975 and 1985 several researchers have investigated the properties of estetrol and reported on its estrogenic potency and uterotrophic activity. The most relevant publications that were issued during this period are mentioned below:

Levine et al., 1984. Uterine vascular effects of estetrol in nonpregnant ewes. Am. J. Obstet. Gynecol., 148:73, 735-738: "When intravenously administered in nonpregnant ewes, estetrol is 15 to 30 times less potent than estriol and 17β-estradiol in uterine vasodilation".

Jozan et al., 1981. Different effects of oestradiol, oestriol, oestetrol and of oestrone on human breast cancer cells (MCF-7) in long term tissue culture. Acta Endocrinologica, 98, 73-80: "Estetrol agonistic potency is 2% of the magnitude observed for 17β-estradiol in in vitro cell proliferation".

Holinka et al., 1980. Comparison of effects of estetrol and tamoxifen with those of estriol and estradiol on the immature rat uterus. Biol. Reprod. 22, 913-926: "Subcutaneously administered estetrol has very weak uterotrophic activity and is considerable less potent than 17β-estradiol and estriol".

Holinka et al., 1979. In vivo effects of estetrol on the immature rat uterus. Biol. Reprod. 20, 242-246: "Subcutaneously administered estetrol has very weak uterotrophic activity and is considerable less potent than 17(3-estradiol and estriol".

Tseng et al., 1978. Heterogeneity of saturable estradiol binding sites in nuclei of human endometrium. Estetrol studies. J. Steroid Biochem. 9, 1145-1148: "Relative binding of estetrol to estrogen receptors in the human endometrium is 1.5% of 17β-estradiol".

Martucci et al., 1977. Direction of estradiol metabolism as a control of its, hormonal action-uterotrophic activity of estradiol metabolites. Endocrin. 101, 1709-1715: "Continuous administration of estetrol, from a subcutaneous depot shows very weak uterotrophic activity and is considerably less potent than 17β-estradiol and estriol".

Tseng et al., 1976. Competition of estetrol and ethynylestradiol with estradiol for nuclear binding in human endometrium. J. Steroid Biochem. 7, 817-822: "The relative binding constant of estetrol binding to the estrogen receptor in the human endometrium is 6.25% compared to 17β-estradiol (100%)".

Martucci et al., 1976. Uterine estrogen receptor binding of catecholestrogens and of estetrol (1,3,5(10)-estratriene-3,15alpha,16alpha,17beta-tetrol). Steroids, 27, 325-333: "Relative binding affinity of estetrol to rat uterine cytosol estrogen receptor is 0.5% of 17β-estradiol (100%). Furthermore, the relative binding affinity of estetrol to rat uterine nuclear estrogen receptor is 0.3% of 17β-estradiol (100%)".

All of the above publications have in common that the authors have investigated the estrogenic potency of estetrol. Without exception they all conclude that estetrol is a weak estrogen. In some of the cited articles the estrogenic potency of estetrol has been found to be lower than that of another biogenic estrogen, namely, 17β-estradiol, which is considered to be a relatively weak estrogen (e.g. compared to ethinyl estradiol). With these findings in mind, it is not surprising that the interest in estetrol has dwindled since the early eighties and that no publications on the properties of estetrol have been issued since.

U.S. Pat. No. 5,468,736 (Hodgen) describes a method of hormone replacement therapy involving the administration of estrogen together with an amount of antiprogestin (antiprogestogen), which inhibits estrogen-induced endometrial proliferation in women. In Example 3 the combined use of estetrol and lilopristone is mentioned. No clues are given in the examples as to the mode and frequency of administration or regarding the dosage level employed. A disadvantage associated with the use of antiprogestogens, such as lilopristone, is the risk of inducing abnormal endometrial morphology, i.e. cystic hyperplasia, as has been observed in women who received an antiprogestogen treatment against endometriosis (Murphy et al., 1995. Fertil. Steril., 95, 761-766).

U.S. Pat. No. 5,340,586 (Pike et al.) is concerned with compositions and methods which are effective to treat oophorectomised women, wherein an effective amount of an estrogenic composition and an androgenic composition are provided over a period of time. In the U.S. patent it is stated that natural and synthetic estrogenic compositions that can be used include natural estrogenic hormones and congeners, including but not limited to estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol and estrone potassium sulfate, and furthermore that equine estrogens, such as equilelinin, equilelinin sulfate and estetrol, may also be employed. Except for the exhaustive inventory of known estrogens, no other reference to estetrol (which is erroneously referred to as an equine estrogen) is made in this U.S. patent.

The same exhaustive list of estrogens is found in the following patent documents:

U.S. Pat. No. 4,762,717 (Crowley): A contraceptive method comprising the sequential administration of (1) a combination of luteinizing hormone releasing hormone (LHRH) and estrogen and (2) a combination of LHRH and estrogen and progestogen.

U.S. Pat. No. 5,130,137 (Crowley): A method of treating benign ovarian secretory disorder comprising the sequential administration of (1) a combination of luteinizing hormone releasing hormone (LHRH) and estrogen and (2) a combination of LHRH and estrogen and progestogen.

U.S. Pat. No. 5,211,952 (Spicer et al.): A contraceptive method comprising administering a gonadotropin hormone releasing hormone (GnRH) composition in an amount effective to inhibit ovulation and administering estrogen and progestogen to maintain serum levels above a defined minimum level.

U.S. Pat. No. 5,340,584 (Spicer et al.): A method for preventing conception or for treating benign gynaecological disorders comprising administering a GnRH composition for a first period of time in an amount effective to suppress ovarian estrogen and progesterone production, simultaneously administering an estrogenic composition in an amount effective to prevent symptoms of estrogen deficiency and simultaneously administering a progestogen in an amount effective to maintain serum level of said progestogen at a level effective to decrease endometrial cell proliferation.

U.S. Pat. No. 5,340,585 (Pike et al.): A method of treating benign gynaecological disorders in a patient in whom the risk of endometrial stimulation by estrogenic compositions is minimised or absent, comprising administering a GnRH composition in an amount effective to suppress ovarian estrogen and progesterone production and administering an estrogenic composition in an amount effective to prevent symptoms of estrogen deficiency.

WO 00/73416 (Yifang et al.): A method for regulating the fertility of a host, comprising contacting host ovarian cells with a safe and effective amount of a pharmaceutical composition comprising an antisense oligonucleotide that is complementary to the nucleotide sequence of the follicle stimulating hormone (FSH) receptor. The possibility of combined administration of such an antisense oligonucleotide with an estrogenic steroid is mentioned in the application.

The benefits of the present invention may be realised without the co-administration of anti-progestogens, LHRH compositions, GnRH compositions and/or antisense oligonucleotides that are complementary to the nucleotide sequence of the follicle stimulating hormone (FSH) receptor as proposed in the aforementioned patents. Also, the present invention may suitably be applied in individuals who have not been oophorectomised, or in whom the risk of endometrial stimulation by estrogenic compositions is not minimised or absent, other than through the co-administration of a progestogen. Furthermore the present method does not require the use of a slow release formulation as is dictated by most of the aforementioned publications.

It is noted that none of the aforementioned publications describe the oral administration of estetrol. The only modes of administration described therein are intravenous and subcutaneous (depot) administration. For each of these modes of administration it can be concluded that the performance of estetrol is very much inferior to that of e.g. 17β-estradiol. Given that there was no reason to assume that a different outcome might be obtained in case of oral administration, it is not surprising that oral administration of estetrol has not been pursued and that no reports to this effect can be found in the prior art.

In view of the low estrogenic potency of the estetrol-like substances that are employed in accordance with the invention, it is surprising that these substances can effectively be used in HRT methods, particularly in HRT methods that employ oral administration of such substances. Although the inventors do not wish to be bound by theory, it is believed that the unexpected efficacy of orally administered estetrol-like substances results from the combination of unforeseen favourable pharmacokinetic (ADME) and pharmacodynamic properties of these substances.

As regards the pharmacokinetic properties of the present estrogenic substances the inventors have discovered that their oral bioavailability is surprisingly high and that their in vivo half-life is considerably longer than that of other biogenic estrogens. Thus, even though estetrol and estetrol-like substances have relatively low estrogenic potency, they may effectively be employed in an oral HRT method because their low potency is compensated for by a relatively high oral bioavailability in combination with a high metabolic stability, as demonstrated by a long half-life.

An important advantage of oral administration of estetrol and estetrol-like substances resides in the fact that the hepatic effects of estetrol-like substances are deemed to be minimal since they are hardly metabolised during the so called "first pass". The first-pass effect of drugs given orally, refers to the process of drug degradation by the liver during a drug's transition from initial ingestion to circulation in the blood stream.

Another advantageous property of the present estrogenic substances resides in the fact that sex hormone-binding globulin (SHBG) hardly binds these estrogenic substances, meaning that, in contrast to most known estrogens, serum levels are representative for bio-activity and independent of SHBG levels.

Yet another important benefit of the present estrogenic substances is derived from their relative insensitivity to interactions with other drugs (drug-drug interactions). It is well known that certain drugs may decrease the effectiveness of estrogens, such as ethinyl estradiol, and other drugs may enhance their activity, resulting in possible increased side-effects. Similarly estrogens may interfere with the metabolism of other drugs. In general, the effect of other drugs on estrogens is due to interference with the absorption, metabolism or excretion of these estrogens, whereas the effect of estrogens on other drugs is due to competition for metabolic pathways.

The clinically most significant group of estrogen-drug interactions occurs with drugs that may induce hepatic microsomal enzymes which may decrease estrogen plasma levels below therapeutic level (for example, anticonvulsant agents; phenyloin, primidone, barbiturates, carbamazepine, ethosuximide, and methosuximide; antituberculous drugs such as rifampin; antifungal drugs such as griseofulvin). The present estrogenic substances are less dependent on up- and downregulation of microsomal liver enzymes (e.g. P450's) and also are less sensitive to competition with other P450 substrates. Similarly, they do not interfere significantly in the metabolism of other drugs.

The conjugates of most estrogens, as formed in the liver, are excreted in the bile and may be broken down by gut bacteria in the colon to liberate the active hormone which can then be reabsorbed (enterohepatic recirculation). There are clinical reports that support the view that enterohepatic recirculation of estrogens decreases in women taking antibiotics such as ampicillin, tetracycline, etc. Conjugated forms of the present estrogenic substances are hardly excreted in the bile, meaning that they are substantially insensitive to drugs that do influence the enterohepatic recirculation of other estrogens.

The above observations serve to explain why the estrogenic substances of the invention hardly suffer from drug-drug interactions and thus produce a very consistent, i.e. predictable, impact. Thus, the efficacy of the estrogenic substances of the invention is highly reliable.

DETAILED DESCRIPTION OF THE INVENTION

Figure 1:
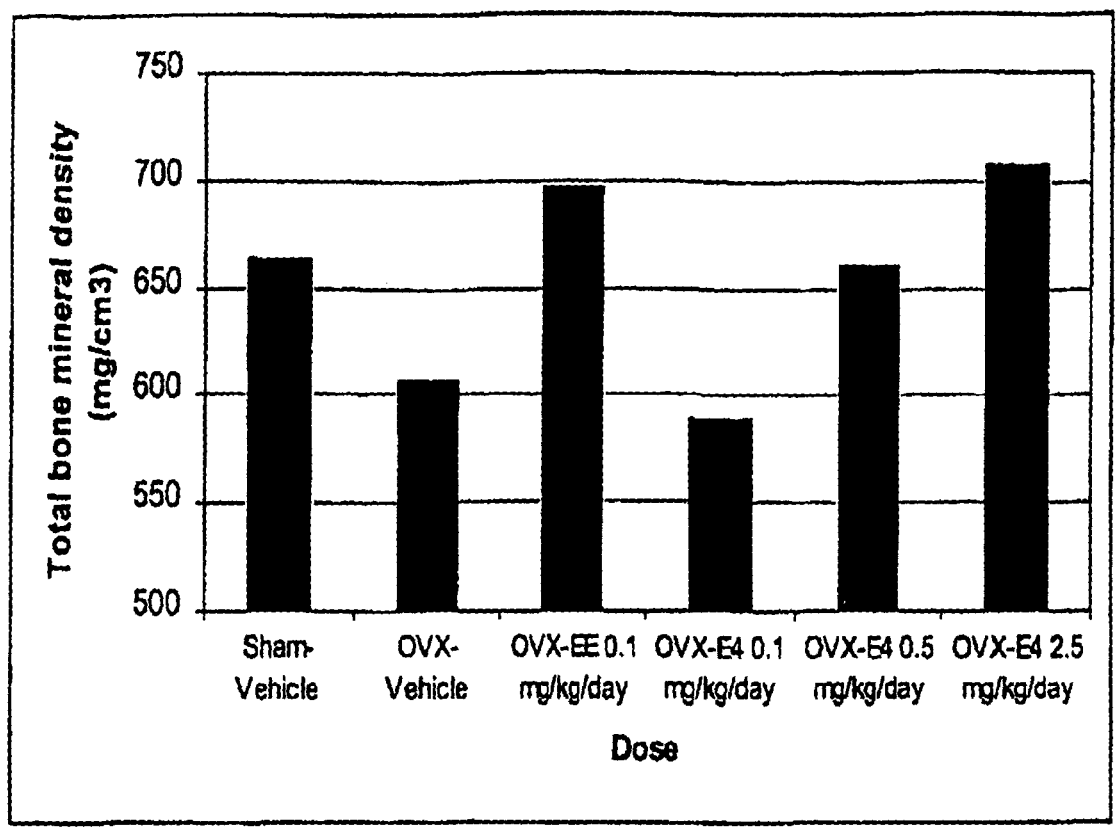
FIG. 1 is a graph showing the total bone mineral density from the proximal tibiae of Sham- and OVX-rats orally (po) treated with 17α-ethinyl estradiol (EE), estetrol (E4) or vehicle for 4 consecutive weeks. Data are expressed as the mean values obtained for each group (n=10).

Accordingly one aspect of the present invention relates to a method of hormone replacement in mammals, which method comprises the oral administration of an estrogenic component and a progestogenic component to a mammal in an effective amount to prevent or treat symptoms of hypoestrogenism, wherein the estrogenic component is selected from the group consisting of:
substances represented by the following formula

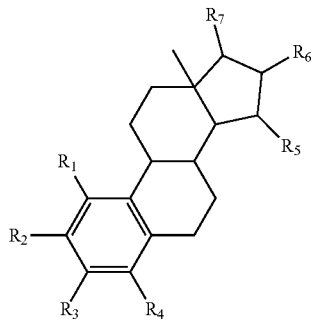

in which, formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; and no more than 3 of $R_1$, $R_2$, $R_3$, $R_4$ are hydrogen atoms;
precursors capable of liberating a substance according to the aforementioned formula when used in the present method; and mixtures of one or more of the aforementioned substances and/or precursors. The term "oral administration" as used in here also encompasses oral gavage administration.

The HRT method according to the invention may advantageously be used to treat all known forms of hypoestrogenism, e.g. hypoestrogenism associated with (peri-)menopausal and post-menopausal women, hypoestrogenism resulting from hypogonadism or castration, as well as hypoestrogenism resulting from primary ovarian failure, treatment of e.g. breast cancer with aromatase inhibitor and gonadotropin-releasing hormone analogue treatment of e.g. benign gynaecological diseases. Examples of manifestations of hypoestrogenism that can effectively be treated or prevented with the present method in both females and males include osteoporosis, arteriosclerosis, cognitive disturbances and Alzheimer's disease. The method may also advantageously be used in the (prophylactic) treatment of climacteric symptoms such as hot flushes (flashes), sweats, urogenital atrophy, mood disturbances, insomnia and palpitations. The present method is particularly suited for treating or preventing osteoporosis and climacteric symptoms.

The term "estrogenic component" as used throughout this document encompasses substances that are capable of triggering an estrogenic response in vivo, as well as precursors that are capable of liberating such an estrogenic component in vivo when used in accordance with the present invention. In order for estrogenic components to trigger such a response they normally have to bind to an estrogen receptor, which receptors are found in various tissues within the mammalian body. The term "progestogenic component" is defined as a substance that is capable of triggering an progestogenic response in vivo or a precursor which is capable of liberating such a substance in vivo. Usually progestogenic components are capable of binding to a progestogen receptor.

It is noted that the present invention not only encompasses the use of estrogenic and progestogenic components specifically mentioned in this application, but also metabolites of these hormones that display comparable in vivo functionality. In this context it is observed that, for instance, levonorgestrel is a metabolite of norgestimate and that estriol is a metabolite of 17beta-estradiol. Both these progestogens and estrogens have found application in contraceptive formulations and/or hormone replacement therapy. The term "estrogenic substances" as used in this document does not encompass tritium ($^3$H) labeled estrogenic substances such as tritium labeled estetrol.

The present estrogenic substances are distinct from both the biogenic and synthetic estrogens that are commonly applied in pharmaceutical formulations in that they contain at least 4 hydroxyl groups. The present substances are special in that the 5 membered ring in the steroid skeleton comprises 3 hydroxyl substituents rather than 0-2.

Known estrogens that contain at least 4-hydroxyl groups and derivatives thereof are:
1,3,5(10)-estratrien-2,3,15α,16α,17β-pentol 2-methyl ether
1,3,5(10)-estratrien-2,3,15β,16α,17β-pentol 2-methyl ether
1,3,5(10)-estratrien-2,3,16α,17β-tetrol
1,3,5(10)-estratrien-3,4,16α,17β-tetrol 4-methyl ether
1,3,5(10)-estratrien-3,15α,16α,17β-tetrol
1,3,5(10)-estratrien-3,15α,16α,17β-tetrol tetra acetate
1,3,5(10)-estratrien-3,15β,16β,17β-tetrol tetra acetate Preferably, the estrogenic substance applied as the active component in the present composition is a natural estrogen, i.e. an estrogen that is found in nature and especially in mammals. Even more preferably, the estrogenic substance is a so called biogenic estrogen, i.e. an estrogen that occurs naturally in the human body, a precursor of a biogenic estrogen or mixtures thereof. Because biogenic estrogens are naturally present in the fetal and female body, side-effects are not expected to occur, particularly not if the serum levels resulting from the exogenous administration of such estrogens do not substantially exceed naturally occurring concentrations. Since estetrol serum levels in the fetus are several times higher than those found in pregnant females and knowing that the fetus is particularly vulnerable, estetrol is deemed to be a particularly safe biogenic estrogen. Side-effects are not expected to occur, particularly not if the serum levels resulting from the exogenous administration of such estrogens do not substantially exceed naturally occurring (fetal) concentrations. With synthetic estrogens such as ethinyl estradiol there is a (dose dependent) risk of undesirable side-effects, such as thromboembolism, fluid retention, nausea, bloating, cholelithiasis, headache and breast pain.

In a preferred embodiment of the present invention the estrogenic substance contains 4 hydroxyl groups. Also, in the aforementioned formula, $R_1$ preferably represents a hydrogen atom. In said formula preferably at least 2, more preferably at least 3 of the groups $R_1$, $R_2$, $R_3$ and $R_4$ represent a hydrogen atom.

The estrogenic substances according to the formula encompass various enantiomers since the carbon atoms that carry hydroxyl-substituents $R_5$, $R_6$ and $R_7$ are chirally active. In one preferred embodiment, the present estrogenic substance is 15α-hydroxy substituted. In another preferred embodiment the substance is 16α-hydroxy substituted. In yet another preferred embodiment, the substances is 17β-hydroxy substituted. Most preferably the estrogenic substances are 15α,16α,17β-trihydroxy substituted.

In another preferred embodiment of the present invention $R_3$ represents a hydroxyl group or an alkoxy group. In another preferred embodiment the groups $R_1$, $R_2$ and $R_4$ represent hydrogen atoms, in which case, if $R_3$, $R_5$, $R_6$ and $R_7$ are hydroxyl groups, the substance is 1,3,5(10)-estratrien-3,15,16,17-tetrol. A preferred isomer of the latter substance is 1,3,5(10)-estratrien-3,15α,16α,17β-tetrol (estetrol).

The invention also encompasses the use of precursors of the estrogenic substances that constitute the active component in the present method. These precursors are capable of liberating the aforementioned estrogenic substances when used in the present method, e.g. as a result of metabolic conversion. These precursors are preferably selected from the group of androgenic precursors as well as derivatives of the present estrogenic substances. Suitable examples of androgenic precursors include androgens that can be converted into the present estrogenic substances through in vivo aromatisation. Examples of derivatives of the present estrogenic substances that can suitably be used as precursors include such substances wherein the hydrogen atom of at least one of the hydroxyl groups has been substituted by an acyl radical of a hydrocarbon carboxylic, sulfonic acid or sulfamic acid of 1-25 carbon atoms; tetrahydrofuranyl; tetrahydropyranal; or a straight or branched chain glycosidic residue containing 1-20-glycosidic units per residue.

Typical examples of precursors which can suitably be used in accordance with the invention are esters that can be obtained by reacting the hydroxyl groups of the estrogenic substances with substances that contain one or more carboxy ($M^{+-}OOC-$) groups, wherein $M^+$ represents a hydrogen or (akali)metal cation. Hence, in a particularly preferred embodiment, the precursors are derivatives of the estrogenic substances, wherein the hydrogen atom of at least one of the hydroxyl groups in said formula has been substituted by —CO—R, wherein R is a hydrocarbon radical comprising from 1-25 carbon atoms. Preferably R is hydrogen, or an alkyl, alkenyl or aryl radical comprising from 1-20 carbon atoms.

The present method usually employs uninterrupted oral administration of the estrogenic component during a period of at least 10 days, preferably of at least 20 days. The term "uninterrupted" as used in here, means that the estrogenic component is administered at relatively regular intervals, with no (therapeutically) significant interruptions. Naturally, minor interruptions may occur that do not affect the overall effectiveness of the present method, and indeed such aberrations are encompassed by the present invention. In a preferred embodiment, and more arithmetically, the administration regimen is deemed to be continuous if the longest interval between 2 subsequent administrations is not more than 3.5 times as long as the average interval. Even more preferably said longest interval is not more than 2.5 times, most preferably not more than 1.5 times as long as the average interval.

The benefits of the present invention are most pronounced when the estrogen component is used in longer term hormone replacement therapy so as to minimise the negative effects of chronic hypoestrogenism. Therefore, the method of hormone replacement therapy, preferably, comprises administering the estrogenic component for a period of at least 1 month, more preferably of at least 3 months.

In the present method, the estrogenic and progestogenic component may be administered in separate oral dosage units. However, it is also possible and indeed very convenient to combine these two components into a single oral dosage unit.

The invention may suitably be reduced to practice in the form of a variety of HRT methods that are known to the person skilled in the art. Amongst these methods are the so called "combined" methods. The combined methods make use of preparations that contain a combination of an estrogen and a progestogen. The combined methods have in common that they are based on a regimen which involves administration of the aforementioned combined preparation, followed by an administration-free interval of about 7 days whereby withdrawal bleeding, simulating the natural menses, occurs. Thus 21 day intervals of hormone administration alternate with 7 days during which no hormones are administered.

As an alternative to the aforementioned combined methods, the so called "sequential" method has been proposed. Typical of the sequential method is that it comprises two consecutive phases, i.e. one phase during which estrogen and no progestogen is administered and another phase during which a combination of estrogen and progestogen is administered. The first sequential methods, like the aforementioned combined methods, made use of an administration free interval of about 7 days. More recently, sequential methods have been proposed which do not include an administration-free (or placebo) period, meaning that estrogen is administered throughout the full cycle and that progestogen is co-administered during only part of that cycle. WO 95/17895 (Ehrlich et al.) describes such an uninterrupted sequential method.

Yet another example of an HRT method which is encompassed by the present invention is the so called "continuous combined" method, which is a particular version of the combined method that uses uninterrupted combined administration of a progestogenic and an estrogenic component during a prolonged period of time, e.g. more than 50 days. In contrast to ordinary combined and sequential methods, no regular menses occur in the continuous combined method as the continuous administration of progestogen in the indicated amounts induces amenorrhoea.

In one embodiment of the invention, which relates to the continuous combined method, the present method comprises the uninterrupted oral administration of the combination of the estrogenic component and the progestogenic component during a period of at least 28, preferably at least 60 days.

In another embodiment of the invention, which relates to sequential and combined methods that employ a significant administration-free interval, the method of the invention comprises an interval of at least 2 days, preferably from 3-9 days, most preferably from 5-8 days, during which no progestogenic component and no estrogenic component is administered and wherein the resulting decrease in serum concentration of the progestogenic component and the estrogenic component induces menses.

Yet another embodiment of the invention, which concerns a sequential method without a significant pause, is characterised in that it comprises the uninterrupted oral administration of the estrogenic component during a period of at least 28 days, preferably at least 60 days, and in that, following the combined administration of the estrogenic component and the progestogenic component, the estrogenic component and no progestogenic component are administered during 3-18 consecutive days, preferably during 5-16 consecutive days and the resulting decrease in serum concentration of the progestogenic component should normally be sufficient to induce menses.

In the present methods uninterrupted administration of the estrogenic component may usually occur at intervals of between 6 hours and 7 days, preferably of between 12 hours and 3 days. The relatively high in vivo half-life of the present estrogenic components in comparison to most known estrogens makes it feasible to employ oral administration intervals that are significantly longer than 1 day. For practical reasons, and particularly with a view to user compliance, it is preferred to orally administer the estrogenic component as well as the progestogenic component at least once daily, most preferably once daily.

In all of the aforementioned methods it is preferred to orally administer the estrogenic component and the progestogenic component at least once daily during a period of at least 10, preferably of at least 20 days. In case of a sequential method without pause or a continuous combined method it is preferred to orally administer the estrogenic component and/or the progestogenic component at least once daily during a period of at least 30 days, more preferably of at least 60 days, most preferably of at least 150 days. Uninterrupted sequential methods, which employ continuous estrogen administration, are characterised by excellent cycle control.

The general concerns about the so called unopposed administration of estrogen, i.e. administration of estrogen without co-administered progestogen might cause hyperplasia of the endometrium, are less applicable to the estrogenic components of the present invention. Therefore, in a particularly preferred embodiment, the present HRT method is executed in accordance with a sequential method without pause.

Good results can be obtained with the present method if the estrogenic component is orally administered in an amount of less than 1 mg per kg of bodyweight per day, preferably of less than 400 µg per kg of bodyweight per day, more preferably of less than 200 µg per kg of bodyweight per day. In order to achieve a significant impact from the administration of the present estrogenic component, it is advisable to orally administer in an amount of at least 1 µg per kg of bodyweight per day. Preferably, the orally administered amount is at least 2 µg per kg of bodyweight per day. More preferably, the orally administered amount is at least 5 µg per kg of bodyweight per day.

In the present method, particularly when used in humans, the estrogenic component is usually administered in an average dosage of at least 0.05 mg per day, preferably of at least 0.1 mg per day. The maximum dosage is normally kept below 40 mg per day, preferably below 20 mg per day. The normally employed dose of the progestogenic component is equivalent to an average oral dosage of 30-750 µg levonorgestrel per day, preferably to an average oral dosage of 50-400 µg levonorgestrel per day.

In the present method, the estrogenic component is preferably administered in an amount effective to achieve a blood serum concentration of at least 1 nanogram per liter, more preferably of at least 10 nanogram per liter, most preferably at least 100 nanogram per liter. Generally the resulting blood serum concentration of the estrogenic component will not exceed 100 µg per liter, preferably it will not exceed 50 µg per liter, more preferably it will not exceed 25 µg per liter.

In accordance with the present invention the progestogenic component is advantageously administered in an amount which is equivalent to a daily oral dosage of 0.3 to 20 µg levonorgestrel per kg of bodyweight, preferably of 0.5-5 µg levonorgestrel per kg of bodyweight.

Examples of progestogens which may suitably be used in accordance with the present invention include: progesterone, levonorgestrel, norgestimate, norethisterone, dydrogesterone, drospirenone, 3-beta-hydroxydesogestrel, 3-keto desogestrel (=etonogestrel), 17-deacetyl norgestimate, 19-norprogesterone, acetoxypregnenolone, allylestrenol, anagestone, chlormadinone, cyproterone, demegestone, desogestrel, dienogest, dihydrogesterone, dimethisterone, ethisterone, ethynodiol diacetate, fluorogestone acetate, gastrinon, gestodene, gestrinone, hydroxymethylprogesterone, hydroxyprogesterone, lynestrenol (=lynoestrenol), medrogestone, medroxyprogesterone, megestrol, melengestrol, nomegestrol, norethindrone (norethisterone), norethynodrel, norgestrel (includes d-norgestrel and dl-norgestrel), norgestrienone, normethisterone, progesterone, quingestanol, (17alpha)-17-hydroxy-11-methylene-19-norpregna-4,15-diene-20-yn-3-one, tibolone, trimegestone, algestone acetophenide, nestorone, promegestone, 17-hydroxyprogesterone esters, 19-nor-17hydroxyprogesterone, 17alpha-ethinyl-testosterone, 17alpha-ethinyl-19-nor-testosterone, d-17beta-acetoxy-13beta-ethyl-17alpha-ethinyl-gon-4-en-3-one oxime and precursors of these compounds that are capable of liberating these progestogens in vivo when used in the present method. Preferably the progestogen used in the present method is selected from the group consisting of progesterone, desogestrel, etonogestrel, gestodene, dienogest, levonorgestrel, norgestimate, norethisterone, drospirenone, trimegestone, dydrogesterone, precursors of these progestogens and mixtures thereof.

The present method also encompasses the co-administration of active principles in addition to the progestogenic and estrogenic component. For instance, androgens may advantageously be co-administered in order to prevent symptoms of hypoandrogenicity. Thus, a preferred embodiment of the invention comprises the co-administration of an androgenic component. The androgenic component is suitably co-administered in an effective amount to suppress symptoms of hypoandrogenicity. Hypoandrogenicity has been associated with mood disturbances, unfavourable changes in haemostatic parameters and lack of bone mass.

The term "androgenic component" is defined as a substance that is capable of triggering an androgenic response in vivo or a precursor which is capable of liberating such a substance in vivo. Usually androgenic components are capable of binding to an androgen receptor.

Androgenic components that may suitably be employed in the present method may be selected from the group consisting of dehydroepiandrosterone (DHEA), danazol, gestrinone, testosterone esters, precursors capable of liberating these androgens when used in the present method and mixtures thereof. Preferably the testosterone esters employed comprise an acyl group which comprises at least 6, more preferably from 8-20 and preferably 9-13 carbon atoms. The androgens that can be used most advantageously in the present method are DHEA and/or testosterone undecanoate.

It is noted that, for instance, DHEA and testosterone undecanoate are precursors of testosterone and that said precursors per se exhibit virtually no affinity for androgen receptors in the female body. The effectiveness of the androgens within the method of the invention is determined by their functionally active form, which may well be different from the form in which they are administered.

In a preferred embodiment the androgen is provided in an amount equivalent to a daily oral dosage of 5 to 250 mg DHEA, which is equivalent to a daily oral dosage of 1 to 50 mg testosterone undecanoate. More preferably the androgen is provided in an amount which is equivalent to a daily oral dosage of 10-120 mg DHEA. Most preferably the androgen is administered in an amount which is equivalent to a daily oral dosage of 20-60 mg DHEA.

In order to obtain the desired impact from the present method it is advisable to administer the dosage units in an amount which leads to an increase in blood serum androgen level of no more than 5 nmole testosterone equivalent per liter, preferably less than 3 nmole testosterone equivalent per liter and most preferably less than 1.5 nmole testosterone equivalent per liter.

The present method preferably does not employ a gonadotropin hormone releasing hormone composition as described in the aforementioned patents U.S. Pat. No. 5,211,952, U.S. Pat. No. 5,340,584 and U.S. Pat. No. 5,340,585. Similarly, the present method preferably does not employ a luteinizing hormone releasing hormone composition as described in U.S. Pat. No. 4,762,717 and U.S. Pat. No. 5,130,137. Furthermore, the present method preferably does not comprise the co-administration of an anti-progestogen as described in U.S. Pat. No. 5,468,736. The method may also suitably be applied without the co-administration of an anti-sense oligonucleotide that is complementary to the nucleotide sequence of the follicle stimulating hormone (FSH) receptor (WO 00/73416).

The present method is preferably not used in oophorectomised females or in females in whom endometrial stimulation by estrogenic compositions is minimised or absent, other than by combined administration of a progestogen and an estrogen, e.g. as a result of hysterectomy.

Another aspect of the invention relates to a pharmaceutical kit comprising at least 20 oral dosage units that contains the estrogenic component as defined herein before and/or the progestogenic component and/or the androgenic component as described herein before, wherein at least 10 units contain between 0.01 and 20 mg, preferably between 0.05 and 10 mg of the estrogenic component, at least 10 units contain the progestogenic component in an amount equivalent to 30-750 μg levonorgestrel and at least 10 dosage units contain the androgenic component in an amount equivalent to 5-250 mg dehydroepiandrosterone.

In the present kit, the estrogenic component may conveniently be combined with the progestogenic component and the androgenic in a single dosage unit. Accordingly, the kit preferably comprises at least 10 dosage units which contain between 0.01 and 20 mg of the estrogenic component, the progestogenic component in an amount equivalent to 30-750 μg levonorgestrel and the androgenic component in an amount equivalent to 5-250 mg dehydroepiandrosterone. A pharmaceutical kit that is particularly suitable for use in combined and sequential methods will usually comprise 20-35 oral dosage units, wherein 10-35 units contain a combination of the estrogenic component and the progestogenic component in the indicated amounts, 0-25 units contain no progestogenic component and the estrogenic component in the indicated amounts, and 0-8 units contain no estrogenic component and no progestogenic component.

A pharmaceutical kit that is particularly suitable for use in a continuous combined regimen or a combined regimen comprises at least 20 oral dosage units which either contain the combination of the progestogenic and the estrogenic component or neither of these two components (placebo's) and of which dosage units at least 15, preferably at least 20 contain the combination of the estrogenic component and the progestogenic component and 0-8 contain no estrogenic component and no progestogenic component. If such a kit is to be used in a continuous combined method, the kit may advantageously comprise at least 28, preferably at least 60 dosage units, all of which dosage units contain the combination of the estrogenic component and the progestogenic component in the amounts indicated above.

In case the present kit is meant to be used in an HRT method that employs an administration free interval so as to induce menses (e.g. a combined method or a sequential method with pause) the kit will usually comprise at least 3 units, preferably at least 5 units that contain no estrogenic component and no progestogenic component.

In a particularly preferred embodiment of the invention the present kit is designed for use in a sequential method. Such a kit will usually comprise 20-35 oral dosage units wherein 10-32 units contain the combination of the estrogenic component and the progestogenic component, and 3-18 units contain the estrogenic component and no progestogenic component. Particularly preferred is a kit that is designed for use in a sequential method without a significant pause. In such a kit, which will usually comprise 20-35 oral dosage units, 10-20 units contain a combination of the estrogenic component and the progestogenic component, 10-18 units contain the estrogenic component and no progestogenic component and at most 1 unit contains no estrogenic component and no progestogenic component.

The pharmaceutical kits according to the present invention will normally contain only one or more of the following types of oral dosage units: units that contain the combination of the estrogenic and the progestogenic component; units that contain the estrogenic component and no progestogenic component; and units that effectively function as placebo's. Preferably the kit comprises at least 20 units that contain the combination of the estrogenic and the progestogenic component or the estrogenic component and no progestogenic component.

If the present kit is to be used in a combined or sequential protocol, the oral dosage units are preferably arranged within the kit in a fixed sequence corresponding to the intended order of administration. Data indications may be provided on the packaging. The packaging may be a tube or box or a strip. The box may be circular, square, or otherwise shaped with the tablets being accommodated separately therein for ease of administration. Date indications may appear adjacent to each tablet corresponding with the days on which each tablet is to be taken. Some indication of the sequence in which the tablets are to be taken preferably appears on the packaging regardless of its form.

Generally speaking, the oral dosage units in the present kit are prepared according to well known pharmaceutical procedures. The active ingredient(s) are combined with a pharmaceutically acceptable excipient and converted into a pharmaceutically acceptable form for oral administration, e.g. a tablet, capsule, cachet, pellet, pill, powder or granules. The excipient may include appropriate pharmaceutical carriers such as diluents, binders and lubricants. For example gums, starches and sugars are commonly used as pharmaceutical carriers. Tablets and other oral dosage units can suitably contain materials such binders (e.g. hydroxypropylmethyl cellulose, polyvinyl pyrrolidine, other cellulosic materials and starch), diluents (e.g. lactose and other sugars, starch, dicalcium phosphate and cellulosic materials), disintegrating agents (e.g. starch polymers and cellulosic materials) and lubricating agents (e.g., stearates and talc).

The active ingredient(s) may comprise from about 0.01% by weight to about 50% by weight of the formulation in the dosage unit, the remainder consisting of excipient. The active ingredient(s) are compounded with the chosen carrier and in for example the case of a tablet form, placed in a tablet moulding apparatus to form the tablets. Alternatively the compounded material may be incorporated as a powder or granules in a capsule. Various other options that may suitably be used in accordance with the present invention are well known to the person skilled in the pharmaceutical art.

The present invention is further illustrated by the following examples, which, however, are not to be construed as limiting. The features disclosed in the foregoing description, in the following examples and in the claims may, both separately and in any combination thereof, be material for realising the invention in diverse forms thereof.

EXAMPLES

Example 1

Vaginal cornification was chosen as a tissue-specific and estrogen-sensitive endpoint to determine the estrogenicity of estetrol (E4), after oral administration, in hypoestrogenic rats. 17α-ethinylestradiol (EE) and vehicle (10% ethanol/sesame oil) served as controls in these bioassays.

Uterine weight increase in the rat is more commonly used as a measure of estrogenicity. However, uterine weight also responds to progesterone, testosterone, and other agents not characteristically regarded as estrogens. In the early 1920s it was discovered that follicular fluid from the pig ovary contained a factor(s) that caused cornification/keratinization of the vaginal epithelium in the rat (Allen and Doisy, 1923, JAMA, 81, 819-821; Allen and Doisy, 1924, Am. J. Physiol., 69, 577-588). The so-called vaginal cornification response in rats subsequently provided a bioassay for testing estrogenicity. Vaginal epithelial cornification/keratinization in ovariectomized rats can be produced only by compounds considered to be true estrogens (Jones et al, 1973, Fert. Steril. 24, 284-291). Vaginal epithelial cornification/keratinization represents, therefore, a highly selective endpoint to determine the potency of estrogens (Reel et al., 1996, Fund. Appli. Toxicol. 34, 288-305).

Adult intact female CD rats were ovariectomized to induce estrogen deficiency. Vaginal lavages were performed daily for seven days to ensure that the rats demonstrated castrate vaginal smears (predominance of leukocytes in the vaginal smear, and similar in appearance to a diestrous vaginal smear). Castrate vaginal smears are indicative that complete ovariectomy was achieved. Treatment commenced following completion of the 7 days of smearing (day 0=first day of dosing). Animals were dosed, once daily for 7 consecutive days. Daily vaginal lavages continued to be obtained for 7 days after dosing was initiated in order to detect vaginal cornification, as an indication of an estrogenic response. A drop of vaginal washings was placed on a glass slide and examined by light microscopy to detect the presence or absence of cornified epithelial cells. Vaginal lavages were obtained prior to dosing on days 0-6 and prior to necropsy on day 7.

The vaginal cornification bioassay was performed in order to determine the estrogenic profile of E4 when given orally (po) to ovariectomized adult rats. EE was used as a positive control. The vehicle (10% ethanol/sesame oil) served as the negative control. Steroids were dissolved in absolute ethanol and then brought to the final concentration with sesame oil (10% ethanol in sesame oil). A vaginal estrogenic response occurred in all rats (8/8) given 50 µg/kg/day EE po by day 7 (Table 1). Similarly, vaginal epithelial cornification was observed in all rats (8/8) treated po with either 0.1, 0.3, 1.0, or 3.0 mg/kg/day E4 by day 7 (Table 1), whereas animals treated with the vehicle did not exhibit vaginal epithelial cornification (0/8). Even in rats given relatively low doses of E4 (e.g. 0.1 and 0.3 mg/kg/day), the onset of vaginal cornification (defined as the amount of animals responding at days 1-3 of the study) was as fast as in EE-treated animals (Table 1), demonstrating estetrol's superb bioavailability characteristics after oral administration.

Table 1: Vaginal estrogenic response in ovariectomized rats treated orally (po) with 17α-ethinyl estradiol (EE) or estetrol (E4). Data are expressed as the number of rats showing vaginal cornification over the number of rats (ratio) treated.

| Treatment Group | Dosing route | Number of Rats Exhibiting Estrogenic Response/Number of Rats Treated Day of Study | | | | | | | |
|---|---|---|---|---|---|---|---|---|---|
| | | Day 0 | Day 1 | Day 2 | Day 3 | Day 4 | Day 5 | Day 6 | Day 7 |
| 0.05 mg/kg/day EE | po | 0/8 | 1/8 | 3/8 | 8/8 | 8/8 | 8/8 | 8/8 | 8/8 |
| Vehicle Control (2 ml/kg/day) | po | 0/8 | 0/8 | 0/8 | 0/8 | 0/8 | 0/8 | 0/8 | 0/8 |
| 0.1 mg/kg/day E4 | po | 0/8 | 0/8 | 1/8 | 7/8 | 8/8 | 8/8 | 8/8 | 8/8 |
| 0.3 mg/kg/day E4 | po | 0/8 | 0/8 | 1/8 | 7/8 | 8/8 | 8/8 | 8/8 | 8/8 |
| 1.0 mg/kg/day E4 | po | 0/8 | 0/8 | 4/8 | 8/8 | 8/8 | 8/8 | 8/8 | 8/8 |
| 3.0 mg/kg/day E4 | po | 0/8 | 0/8 | 6/8 | 8/8 | 8/8 | 8/8 | 8/8 | 8/8 |

Example 2

The ovariectomized aged rat was used as a model for the human disease osteoporosis. This is an established animal model, recommended by the United States Food and Drug Administration (FDA), to evaluate and assess potential agents for osteoporosis prevention and therapy. The anti-resorptive efficacy of estetrol (E4) was tested by ex vivo measuring total and trabecular bone mineral density and bone strength after 4 weeks of treatment at necropsy. 17α-ethinyl-estradiol (EE) and vehicle (1% ethanol/arachidis oil) served as controls in this bioassay.

Three months old female Sprague-Dawley rats were either sham-operated (Sham) or ovariectomized (OVX) one day prior to commencement of the dosing study. Animals were anesthetized using a ketamine/xylazine anesthetic mixture and underwent a bilateral ovariectomy or were sham-treated. A section of hair on the dorsal surface was shaved and an incision made overlying the lumbar region of the spine. The skin was separated from the underlying fascia so that a second incision could be made through the abdominal musculature approximately caudal to the kidneys. The ovaries were then exteriorized and removed and the musculature was closed with a single suture. The skin incision was closed using surgical staples.

Ten animals per treatment group were orally dosed once per day for four consecutive weeks. The dosing commenced 1 day after surgical removal of the ovaries and was administered by oral gavage using a syringe and stainless steel gavage needle at doses of 0.1 mg/kg/day EE, or either 2.5, 0.5 or 0.1 mg/kg/day E4. Vehicle control was daily administered to one group of OVX-animals and sham-operated rats. After treatment, anesthetized rats were subjected to cardiac puncture and asphyxiated by $CO_2$ inhalation. Tibiae and femura were removed, cleaned of soft-tissue and fixed and stored in 70% ethanol/saline at 4° C. (tibia) or saline at 4° C. (femura) until further analysis.

Ex vivo peripheral Quantitative Computed Tomography (pQCT) was performed on the excised left tibiae using a Stratec XCT-RM and associated software (Stratec Medizintechnik GmbH, Pforzheim, Germany, software version 5.40). The scans were performed at 12% of the total length from the proximal end of the tibiae. The positions were verified using scout views and one 0.5-mm slice perpendicular to the long axis of the tibial shaft was acquired from each site. The scans were analyzed using a threshold for delineation of the external boundary. The total and trabecular bone mineral content, area and density at each site were determined. Mean values are shown in Table 2. Furthermore, pQCT data for mean total bone mineral density are depicted in FIG. 1.

Table 2: pQCT densitometry data from the proximal tibiae of Sham- and OVX-rats orally (po) treated with 17α-ethinyl estradiol (EE), estetrol (E4) or vehicle. Data are expressed as the mean values obtained for each group (n=10).

Comparison of the pQCT densitometry data from the proximal tibiae of Sham-operated and OVX-rats demonstrated a consistent loss of total and trabecular bone in the OVX-group, as expected (Table 2, FIG. 1). Furthermore, there was a consistent dose-dependent increase for each of the parameters associated with total and trabecular bone mineral content and bone mineral density in the animals orally treated with E4 (Table 2, FIG. 1). As compared to hypoestrogenic OVX-rats receiving vehicle treatment alone, 0.5 and 2.5 mg/kg/day E4 prevented bone resorption as exemplified by total bone mineral density levels equivalent to sham-operated rats (FIG. 1). Furthermore, the anti-resorptive activity achieved with the highest dose of E4 (2.5 mg/kg/day) was equivalent to the effect seen with the positive control EE.

Ex vivo evaluation of bone biomechanical strength was performed with an indentation test at the distal femura. Prior to mechanical testing femura were rinsed in cold saline and carefully cleaned of any remaining adherent soft tissue. A 3-mm segment of the distal femoral metaphysis was cut directly proximal to the femoral condyle with a low-speed diamond saw under constant saline irrigation. The load was applied with a cylindrical indenter (with a flat testing face of 1.6 mm diameter) to the center of marrow cavity on the distal face of the segment. The indenter was allowed to penetrate the cavity at a constant displacement of 6 mm/min to a depth of 2 mm before load reversal.

Table 3: Indentation testing of the distal femur of Sham- and OVX-rats orally (po) treated with 17α-ethinyl estradiol (EE), estetrol (E4) or vehicle. Data are expressed as the mean values obtained for each group (n=10).

| Treatment Group (n = 10) | Dosing route | Maximum load (N) | Stiffness (N/mm) | Energy (mJ) | Ultimate strength (N/mm2) |
|---|---|---|---|---|---|
| SHAM + Vehicle | po | 8.61 | 131.96 | 0.48 | 4.57 |
| OVX + Vehicle | po | 2.77 | 42.08 | 0.21 | 1.47 |
| OVX + 0.1 mg/kg/day EE | po | 9.05 | 169.12 | 0.53 | 4.80 |
| OVX + 0.1 mg/kg/day E4 | po | 1.50 | 28.00 | 0.09 | 0.80 |
| OVX + 0.5 mg/kg/day E4 | po | 7.25 | 132.57 | 0.31 | 3.85 |
| OVX + 2.5 mg/kg/day E4 | po | 13.07 | 173.12 | 0.68 | 6.94 |

| Treatment Group (n = 10) | Dosing route | Mean Total Bone Mineral | | | Mean Trabecular Bone Mineral | | |
|---|---|---|---|---|---|---|---|
| | | Content (mg/mm) | Area (mm$^2$) | Density (mg/cm$^3$) | Content (mg/mm) | Area (mm$^2$) | Density (mg/cm$^3$) |
| SHAM + Vehicle | po | 9.36 | 14.10 | 664.07 | 1.49 | 6.34 | 235.48 |
| OVX + Vehicle | po | 8.76 | 14.47 | 606.61 | 1.10 | 6.51 | 169.63 |
| OVX + 0.1 mg/kg/day EE | po | 9.66 | 13.87 | 697.48 | 1.81 | 6.24 | 290.16 |
| OVX + 0.1 mg/kg/day E4 | po | 8.46 | 14.41 | 588.62 | 0.96 | 6.48 | 145.46 |
| OVX + 0.5 mg/kg/day E4 | po | 9.74 | 14.80 | 660.57 | 1.60 | 6.65 | 243.31 |
| OVX + 2.5 mg/kg/day E4 | po | 9.61 | 13.59 | 707.11 | 1.89 | 6.12 | 309.58 |

Figure 2:
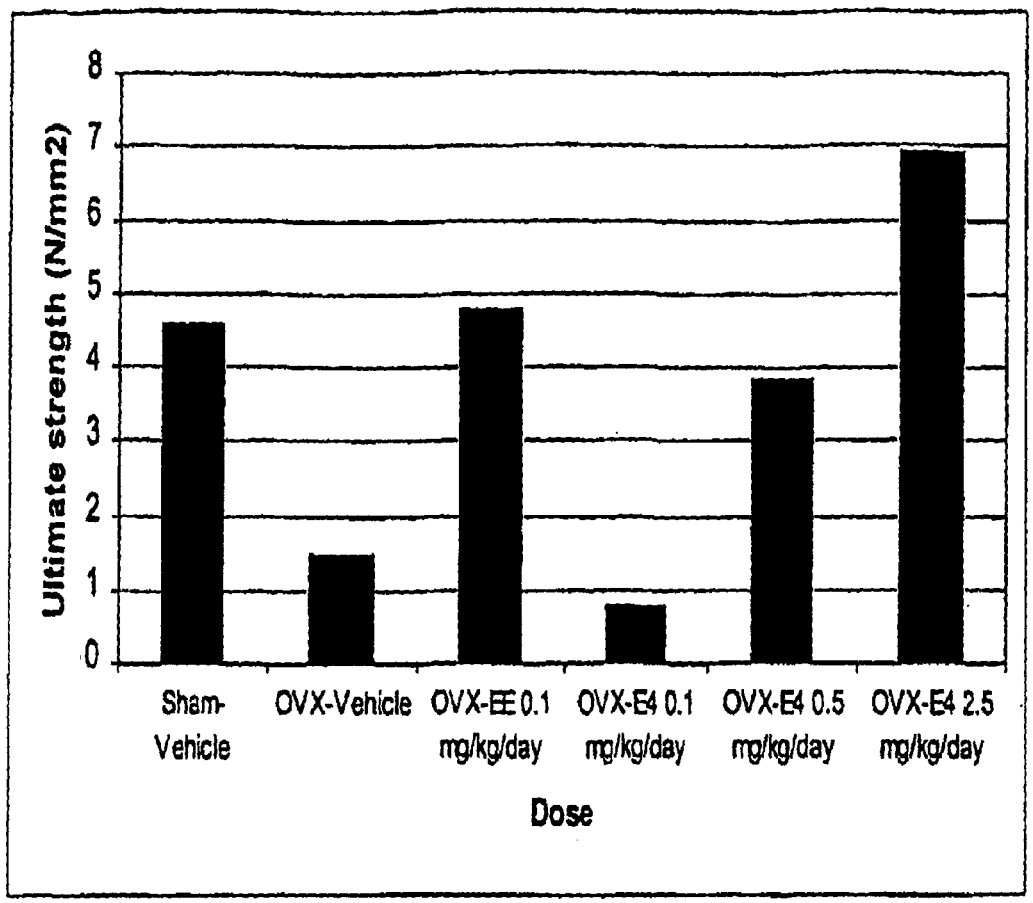
FIG. 2 is a graph showing the mean ultimate strength of the distal femur of Sham- and OVX-rats orally (po) treated with 17α-ethinyl estradiol (EE), estetrol (E4) or vehicle for 4 consecutive weeks. Data are expressed as the mean values obtained for each group (n=10).

The maximum load, stiffness and energy absorbed were determined from load displacement curves. Ultimate strength was calculated by dividing the maximum load by the indenter area. Mean values of maximum load, stiffness, energy and ultimate strength are shown in Table 3. Furthermore, mean ultimate strength values are depicted in FIG. 2. As compared to Sham-operated rats, the mechanical strength of cancellous bone appeared to be markedly reduced in OVX-rats treated with vehicle alone (Table 3, FIG. 2). Reductions in maximum load, stiffness, energy and ultimate strength were −68%, −68%, −27% and −68%, respectively, clearly accompanying the bone mineral density loss in estrogen deficient rats. Oral treatment of hypoestrogenic OVX-rats with E4 prevented the declines in maximum load, stiffness, energy and ultimate strength, in a dose-dependent manner (Table 3, FIG. 2). In addition, the efficacy achieved with the highest doses of E4 (2.5 mg/kg/day) even appears superior to that of the positive control EE (Table 3, FIG. 2).

Example 3

The morphine-dependent ovariectomized (OVX) rat was used as a model for postmenopausal hot flush. The potency of estetrol (E4) to prevent tail skin temperature rises, normally accompanied by a drop in core body temperature, after naloxone-induced opiate withdrawal was tested. 17α-ethinyl-estradiol (EE) and vehicle (hydroxy propyl-beta-cyclodextrin 20% wt/vol) served as controls in this bioassay.

The most common and characteristic symptom of human menopause is the hot flush, which is experienced by over 70% of menopausal females. While the exact mechanism underlying this vasomotor instability is unknown, the characteristic features of the hot flush appear to reflect a centrally mediated adaptation to a progressive decline in the levels of estrogens. In women experiencing the hot flush the symptoms are manifested by 1) rapid, regional elevations in skin temperature; 2) a decrease in core body temperature; 3) an increased heart rate with no change in blood pressure; and 4) closely timed surges in release of luteinizing hormone (LH) and β-endorphin.

The morphine-dependent ovariectomized (OVX) rat model has been proposed by several investigators (Katovich et al, 1986, Maturitas, 67-76; Merchenthaler et al. 1998, Maturitas, 307-316) as an animal model for the hot flush. During opiate withdrawal with the morphine antagonist naloxone, tail skin temperature (TST) rises and this rise is accompanied by a drop in core body temperature. In addition, the temperature changes are accompanied by surges in LH and a transient tachycardia. These events are similar in magnitude and temporal nature to those observed in the menopausal hot flush.

8-week-old OVX rats were treated orally (po) with estetrol (E4), 17α-ethinyl estradiol (EE) or vehicle control (hydroxy propyl-beta-cyclodextrin 20% wt/vol) for seven consecutive days prior to, and on the morning of naloxone-induced opiate withdrawal in morphine-dependent animals. Three days prior to the commencement of dosing, animals were anesthetized using a ketamine/xylazine anesthetic mixture and underwent a bilateral ovariectomy. A section of hair on the dorsal surface was shaved and an incision made overlying the lumbar region of the spine. The skin was separated from the underlying fascia so that a second incision could be made through the abdominal musculature approximately caudal to the kidneys. The ovaries were then exteriorized and removed and the musculature was closed with a single suture. The skin incision was closed using surgical staples. Six rats per treatment group were dosed once per day for eight consecutive days prior to and including the day of naloxone-induced opiate withdrawal (the hot flush session). The dosing commenced three days after surgical removal of the ovaries and was administered by oral gavage using a syringe and stainless steel gavage needle. Morphine dependency was induced by implantation of subcutaneous pellets containing 75-mg morphine. The first pellet was implanted five days before the hot flush session under a light inhalation anesthesia. Three days before the hot flush session, two additional morphine pellets were implanted under the same conditions.

For the hot flush manipulations the animals were placed in a test cage. Following a 5-10 minute adaptation period, the rats were anesthetized with ketamine HCl approximately 10 minutes prior to the hot flush session. A temperature sensitive electrode was fixed to the ventral surface of the tail with tape and the electrode was connected to a multi-channel temperature recorder. The tail-skin temperature was recorded until it was stable and the animals were then injected with naloxone HCl (1 mg/kg). The temperature recordings then continued for a period of 60 minutes and the temperature was reported at 5-minute intervals. At the completion of the hot flush session, all animals were killed using $CO_2$ asphyxiation followed by cervical dislocation.

Figure 3:
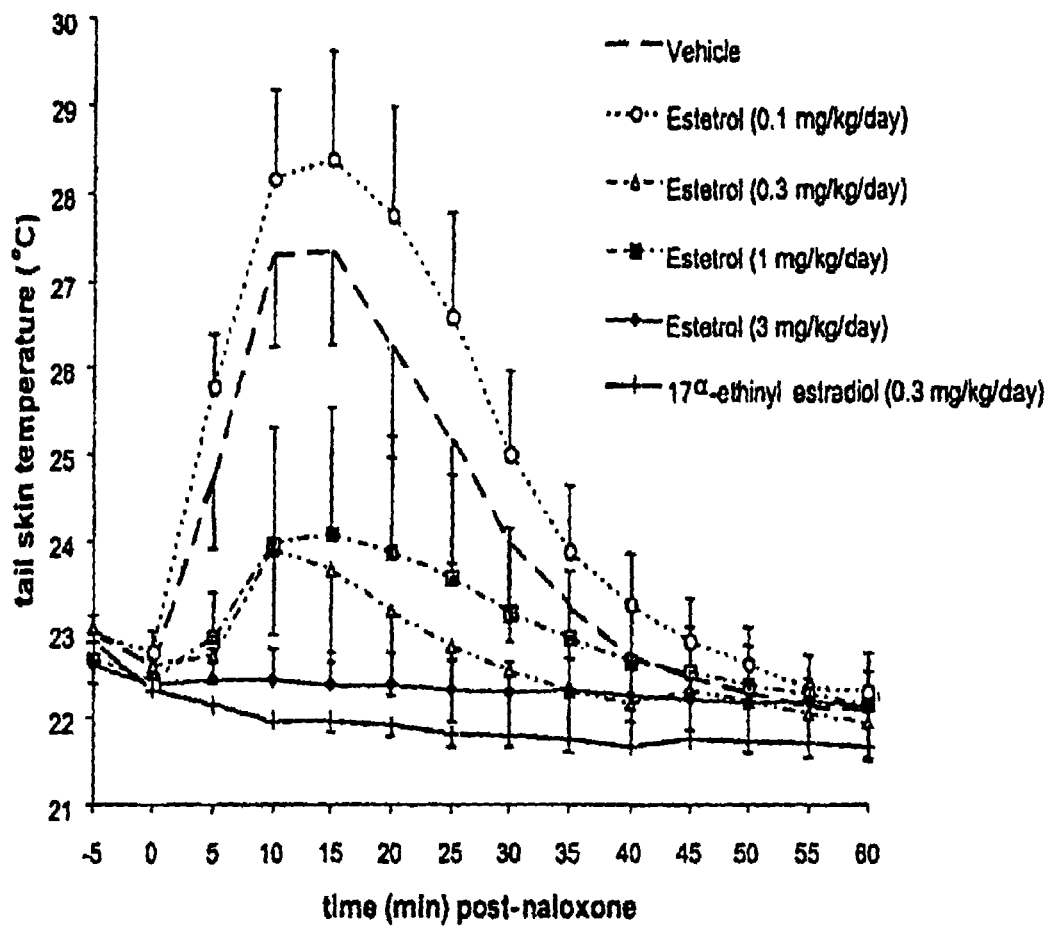
FIG. 3 is a graph showing the effects of estetrol (E4) and 17α-ethinyl estradiol (EE) on the malonxone induced hot flush response in female ovariectomized rats.

As expected, vehicle control was ineffective in preventing the naloxone-induced TST increases in the morphine addicted OVX rats (FIG. 3). 17α-ethinyl estradiol (EE), at the single dose tested of 0.3 mg/kg/day, prevented the naloxone-induced TST increases in the morphine addicted OVX rats (FIG. 3). Oral treatment with estetrol (E4) showed a clear dose-dependent effect (FIG. 3). The three highest doses of E4 (0.3, 1.0 and 3.0 mg/kg/day) all attenuated the TST, with the highest dose (3.0 mg/kg/day) having a suppressive response similar to the potent oral estrogen, 17α-ethinyl estradiol (EE).

Example 4

To evaluate the oral bioavailability of estetrol (E4) and to determine the elimination half-life, single oral (po) and subcutaneous (sc) dose studies were performed in female Sprague Dawley rats followed by frequent blood sampling over a 24 hours interval.

Female Sprague Dawley rats were equipped with a permanent silatic heart catheter, as described by Kuipers et al. (1985, Gastroenterology, 88, 403-411). Rats were allowed to recover from surgery for 5 days and were than administered 0.05, 0.5, or 5 mg/kg E4 in 0.5 ml arachidis oil. For sc administration, E4 was injected in the neck area using a 1 ml syringe and 20 g needle. For po administration of E4, rats were lightly anaesthesized with halothene/$N_2O/O_2$ and E4 was directly applied intragastrically using a plastic stomach intubator. Blood samples were subsequently collected via the heart catheter in heparinized tubes at 0.5, 1, 2, 4, 8 and 24 hours. Erythrocytes were removed by centrifugation at 5000×g for 10 minutes at 4° C. and blood plasma was stored at −20° C. After thawing the plasma samples, liquid-liquid extraction (hexane and diethyl ether) was employed to prepare the E4-containing plasma samples for HPLC analysis (Perkin Elmer 200) and tandem mass spectrometry using a PE Sciex 3000 tandem mass spectrometer and APCI interface. With each sample batch, a calibration curve with 6 calibrators was recorded. The calibration curve was calculated using linear regression (correlation coefficient >0.98), which permitted quantitation of plasma concentrations. For each rat plasma, sampled at different time intervals, data were collected.

Plasma E4 concentration data were analysed with "WinNonLin, edition 3.1" and involved pharmacokinetic parameters for $C_{max}$, half-life and $AUC_{0-24}$. Especially, using the lower and intermediate dose levels of 0.05, 0.5 mg/kg, E4 demonstrated an oral bioavailability equal to the bioavailability obtained with sc administration (80-100%). At the highest dose level tested, 5.0 mg/kg E4, absorption kinetics gave rise to an oral bioavailability approximating 30-60% of sc administered E4. Interestingly, E4 demonstrated a relatively long half-life of 2-3 hours, enabling the detection of bioactive levels of unconjugated E4 at all time points over a 24 hour interval.

Example 5

An established competitive steroid-binding assay (Hammond and Lahteenmaki. 1983. Clin Chem Acta 132:101-110) was used to determine the relative binding affinity of estetrol (E4), 17α-ethinylestradiol (EE2), 17β-estradiol (E2), testosterone (T) and 5α-dihydrotestosterone (DHT) for human sex Hormone Binding Globulin (SHBG).

Human SHBG was purified from transgenic mouse serum, as described previously (Avvakumov G V et al., 2000. J Biol Chem 275: 25920-25925). The human SHBG prepared in this way was assessed to be >99% pure by polyacrylamide gel electrophoresis under denaturing conditions. Its steroid-binding characteristics are indistinguishable from SHBG in human serum (Avvakumov G V et al., 2000. J Biol Chem 275: 25920-25925). The in vitro assay involved the use of the purified human SHBG and [$^3$H]DHT or [$^3$H]estradiol as labeled ligands. Human SHBG was treated for 30 min at room temperature with a dextran-coated charcoal (DCC) suspension in phosphate buffered saline (PBS) to remove any steroid ligand. After centrifugation (2,000×g for 10 min) to sediment the DCC, the supernatant containing the human SHBG was diluted in PBS to a concentration of 1 nM based on its steroid binding capacity.

Duplicate aliquots (100 μl) of this human SHBG solution were then incubated with an equal volume of either [$^3$H]DHT or [$^3$H]estradiol at 10 nM, together with 100 μl of PBS alone or the same amount of PBS containing increasing concentrations of unlabeled steroid ligands as competitors in polystyrene test tubes. After incubation for 1 h at room temperature the reaction mixtures were placed in an ice bath for a further 15 min. Aliquots (600 μl) of an ice cold suspension of DCC were then added to each tube, and after a brief 2 seconds mixing, each tube was incubated in an ice bath for either 10 min or 5 min depending on whether [$^3$H]DHT or [$^3$H]estradiol were being used as labeled ligands, respectively. The unbound ligands adsorbed to DCC were then removed by centrifugation (2,000×g for 15 min at 4 C), and the amounts of [$^3$H]labeled ligands bound to SHBG were counted in 2 ml ACS scintillation cocktail using in liquid scintillation spectrophotometer. The average amounts of [$^3$H]labeled ligands bound to SHBG at each concentration of competitor (B) were expressed as a percentage of the average amounts of [$^3$H] labeled ligands bound to SHBG in the absence of competitor ($B_0$), and were plotted against the concentration of competitor in each assay tube.

Figure 4:
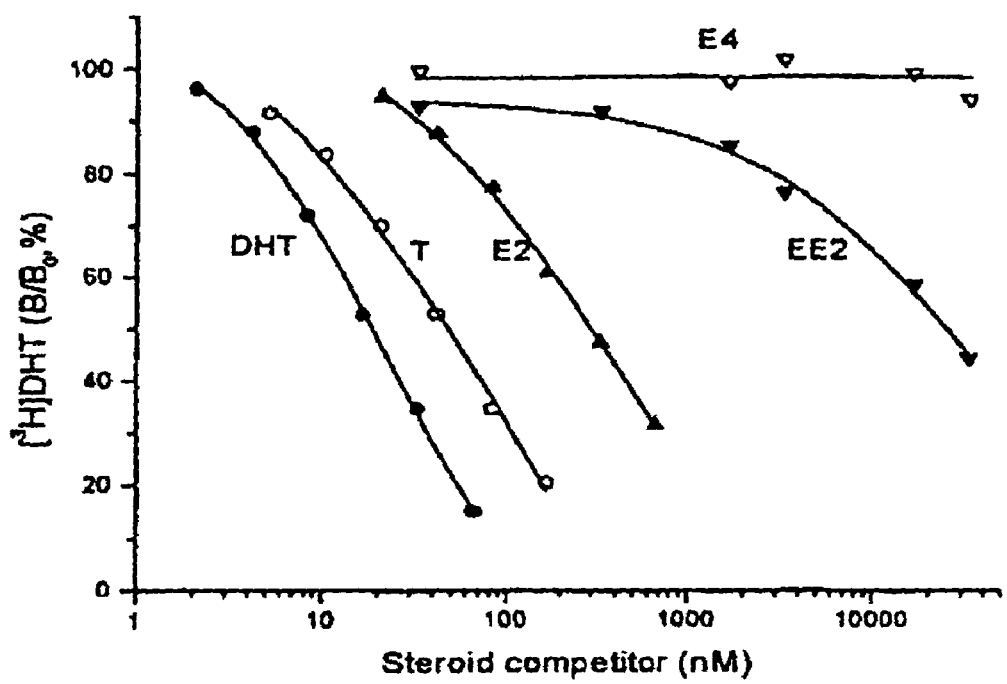
FIG. 4 contains graphs showing the competitive displacement of [$^3$H]DHT (panel A) and [$^3$H]estradiol (panel B) from the human sex hormone-binding globulin steroid binging site. The unlabeled steroid ligands used as competitors were as follows: estetrol (E4), 17α-ethinyl estradiol (EE2), 17β-estradiol (E2), testosterone (T) and 5α-dihydrotestosterone (DHT).
Figure 4:
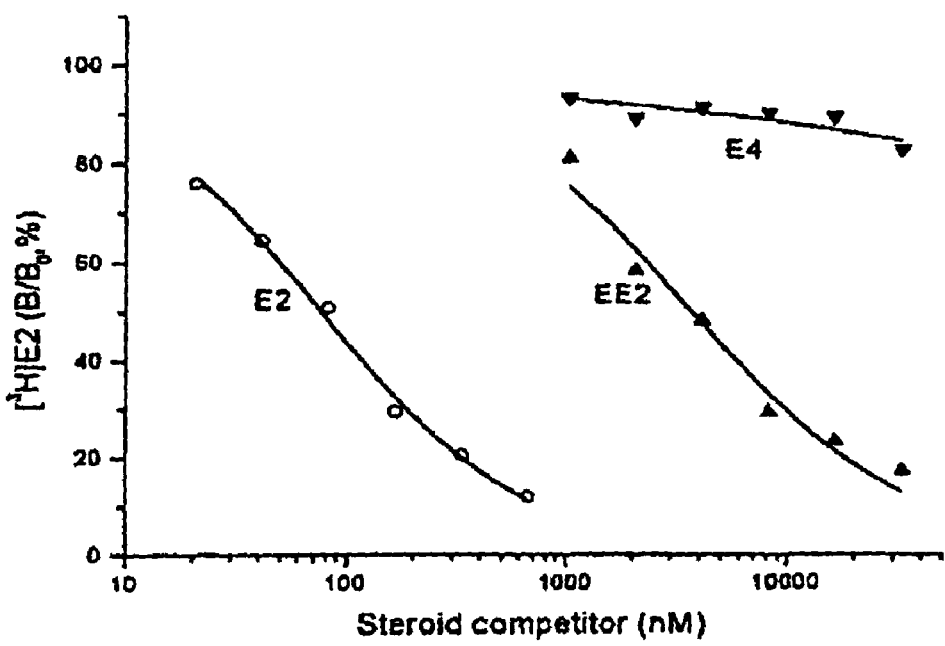

The results of the competitive binding assays are depicted in FIG. 4. As is clearly apparent from these competitive binding assays, estetrol does not bind at all to human SHBG when tested with either [$^3$H]DHT or [$^3$H]estradiol as labeled ligands. This is in marked contrast with reference steroids ethinylestradiol, 17β-estradiol, testosterone and 5α-dihydrotestosterone, which, in this order, show an increased relative binding affinity for human SHBG. Importantly, estetrol binding to SHBG was negligible when compared with the other estrogens tested, ethinylestradiol and 17β-estradiol.

Example 6

The present estrogenic components may suitably be processed, together with additives, excipients and/or flavouring agents customary in galenic pharmacy, in accordance with the conventional methods into the usual forms of administration. For oral administration, suitable are, in particular, tablets, dragees, capsules, pills, suspensions, or solutions.

Estetrol tablets: 1,000 tablets of 185 mg, containing 1.5 mg estetrol and 0.15 mg levonorgestrel, are produced from the following formulation:

| | |
|---|---|
| Estetrol | 1.500 g |
| Levonorgestrel | 0.150 g |
| Polyvinylpyrrolidone (Kollidon 25® ex BASF) | 13.500 g |
| Lactose | 135.645 g |
| Microcrystalline cellulose (Avicel PH 101®) | 26.250 g |
| Glyceryl palmitostearate (Precirol ®) | 2.775 g |
| Anhydrous colloidal silica (Aerosil 200®) | 1.000 g |
| Crospovidone (Polyplasdone XL® ) | 4.000 g |
| Coloring agent | 0.180 g |

Tablets that additionally contain 50 mg dehydroepiandrosterone may be prepared from a similar formulation.

What is claimed is:

1. A method of hormone replacement in mammals comprising orally administering an estrogenic component and a progestogenic component to a mammal in an effective amount to treat symptoms of hypoestrogenism, the estrogenic component being selected from the group consisting of estetrol;

precursors capable of liberating estetrol when used in the present method, which precursors are derivatives of estetrol, wherein the hydrogen atom of at least one of the hydroxyl groups has been substituted by an acyl radical of a hydrocarbon carboxylic, sulfonic or sulfamic acid of 1-25 carbon atoms; tetrahydrofuranyl; tetrahydropyranal; or a straight or branched chain glycosidic residue containing 1-20 glycosidic units per residue; and mixtures of estetrol and the precursors.

2. The method according to claim 1, wherein the symptoms of hypoestrogenism are selected from the group consisting of osteoporosis, arteriosclerosis, climacteric symptoms, cognitive disturbances and Alzheimer's disease.

3. The method according to claim 1, wherein the method comprises the daily oral administration of the estrogenic component during a period of at least 10 days.

4. The method according to claim 3, wherein the method comprises the daily oral administration, during a period of at least 10 days, of a combination of the estrogenic component and a progestogenic component.

5. The method according to claim 4, wherein the method comprises the daily oral administration of the combination of the estrogenic component and the progestogenic component during a period of at least 28 days.

6. The method according to claim 4, wherein the method further comprises an interval of at least 2 days during which no progestogenic component and no estrogenic component is administered and wherein the resulting decrease in serum concentration of the progestogenic component and the estrogenic component induces menses.

7. The method according to claim 4, wherein the method comprises the daily oral administration of the estrogenic component during a period of at least 28 days and wherein, following the combined administration of the estrogenic component and the progestogenic component, the estrogenic component and no progestogenic component are administered during 3-18 consecutive days and the resulting decrease in serum concentration of the progestogenic component induces menses.

8. The method according to claim 1, wherein the method comprises the at least once daily oral administration of the estrogenic component and the progestogenic component during a period of at least 10 days.

9. The method according to claim 1, wherein the estrogenic component is orally administered in an amount of less than 1 mg per kg of bodyweight per day.

10. The method according to claim 1, wherein the estrogenic component is orally administered in an amount of at least 1 µg per kg of bodyweight per day.

11. The method according to claim 1, wherein the progestogenic component is administered in an amount which is equivalent to a daily oral dosage of 0.3 to 20 µg levonorgestrel per kg of bodyweight.

12. A pharmaceutical kit comprising at least 20 oral dosage units that contain the estrogenic component as defined in claim 1 and/or the progestogenic component as defined in claim 1 and/or an androgenic component, wherein at least 10 units contain between 0.01 and 20 mg of the estrogenic component, at least 10 units contain the progestogenic component in an amount equivalent to 30-750 µg levonorgestrel and at least 10 dosage units contain the androgenic component in an amount equivalent to 5-250 mg dehydroepiandrosterone.

13. The pharmaceutical kit according to claim 12, comprising at least 10 oral dosage units that contain between 0.01 and 20 mg of the estrogenic component, the progestogenic component in an amount equivalent to 30-750 µg levonorgestrel and the androgenic component in an amount equivalent to 5-250 mg dehydroepiandrosterone.

14. The pharmaceutical kit according to claim 12, wherein the androgenic component is selected from the group consisting of dehydroepiandrosterone (DHEA), danazol, gestrinone, testosterone esters, precursors capable of liberating these androgens when used in the present method and mixtures thereof.

* * * * *